US009155280B2

(12) United States Patent
Gibson

(10) Patent No.: US 9,155,280 B2
(45) Date of Patent: Oct. 13, 2015

(54) MONDO LETTUCE VARIETY

(71) Applicant: PROGENY ADVANCED GENETICS, Salinas, CA (US)

(72) Inventor: Darryn Gibson, Prunedale, CA (US)

(73) Assignee: Progeny Advanced Genetics, Salinas, CA (US)

( * ) Notice: Subject to any disclaimer, the term of this patent is extended or adjusted under 35 U.S.C. 154(b) by 279 days.

(21) Appl. No.: 13/831,030

(22) Filed: Mar. 14, 2013

(65) Prior Publication Data

US 2014/0047584 A1 Feb. 13, 2014

Related U.S. Application Data

(60) Provisional application No. 61/681,495, filed on Aug. 9, 2012.

(51) Int. Cl.
*A01H 5/12* (2006.01)

(52) U.S. Cl.
CPC ........................................ *A01H 5/12* (2013.01)

(58) Field of Classification Search
None
See application file for complete search history.

(56) References Cited

U.S. PATENT DOCUMENTS 8,278,509 B2 * 10/2012 Gibson ......................... 800/305

* cited by examiner

*Primary Examiner* — Eileen B O Hara
(74) *Attorney, Agent, or Firm* — Morrison & Foerster LLP

(57) ABSTRACT

A new lettuce variety designated ‘Mondo’ is described. ‘Mondo’ is a romaine lettuce variety exhibiting stability and uniformity.

11 Claims, No Drawings

MONDO LETTUCE VARIETY

CROSS REFERENCE TO RELATED APPLICATION

This application claims the benefit under 35 §USC 119(e) of prior U.S. Provisional Patent Application No. 61/681,495, filed Aug. 9, 2012, the disclosure of which is hereby incorporated by reference in its entirety.

FIELD

This invention relates to the field of plant breeding. In particular, this invention relates to new lettuce, *Lactuca sativa*, variety, 'Mondo'.

BACKGROUND

Lettuce is an increasingly popular crop. Worldwide lettuce consumption continues to increase. As a result of this demand, there is a continued need for new lettuce varieties. In particular, there is a need for improved romaine lettuce varieties that exhibit improved growth habits, bolting and tip burn tolerance, and disease resistance.

SUMMARY

In order to meet these needs, the present invention is directed to an improved romaine lettuce variety with a medium to light green color and open to cupping growth habit that forms an open to very dense heart, and improved tolerance to bolting and tip burn, as well as resistance to Tomato Bushy Stunt Virus (Tombusvirus), *Sclerotinia* (*S. minor*), and Corky Root (*Rhizomonas suberifaciens*). In particular, the present invention is directed to lettuce, *Lactuca sativa*, seed designated as 'Mondo' having ATCC Accession Number PTA-120397. The present invention is further directed to a lettuce head isolated from a *Lactuca sativa* plant produced by growing 'Mondo' lettuce seed having ATCC Accession Number PTA-120397. The present invention is further directed to a *Lactuca sativa* plant having all the physiological and morphological characteristics of a *Lactuca sativa* plant produced by growing 'Mondo' lettuce seed having ATCC Accession Number PTA-120397. The present invention is further directed to an $F_1$ hybrid *Lactuca sativa* plant having 'Mondo' as a parent, where 'Mondo' lettuce seed is grown from 'Mondo' seed having ATCC Accession Number PTA-120397.

The present invention is further directed to lettuce, *Lactuca sativa* plants and lettuce heads isolated therefrom produced by growing 'Mondo' lettuce seed. The present invention is further directed to a *Lactuca sativa* plant and the lettuce head isolated therefrom having all the physiological and morphological characteristics of a *Lactuca sativa* plant produced by growing 'Mondo' lettuce seed having ATCC Accession Number PTA-120397. The present invention is further directed to an $F_1$ hybrid lettuce, *Lactuca sativa* plant and a head isolated therefrom grown from the seed having 'Mondo' as a parent wherein 'Mondo' is grown from 'Mondo' lettuce seed having ATCC Accession Number PTA-120397.

The present invention is further directed to pollen isolated from 'Mondo' lettuce plants. The present invention is further directed to ovules isolated from 'Mondo' lettuce plants. The present invention is further directed to tissue culture of 'Mondo' lettuce plants.

The present invention is further directed to a method of selecting lettuce plants by: a) growing more than one 'Mondo' lettuce plant, where the plants are grown from lettuce seed having ATCC Accession Number PTA-120397; and b) selecting a plant from step a). The present invention is further directed to lettuce plants and seeds produced therefrom, where the lettuce plants and seeds are isolated by the selection method of the invention.

The present invention is further directed to a method of breeding lettuce by crossing a lettuce plant with a plant grown from 'Mondo' lettuce seed having ATCC Accession Number PTA-120397. The present invention is further directed to lettuce plants, heads isolated therefrom, and seeds produced therefrom, where the lettuce plant is isolated by the breeding method of the invention.

DETAILED DESCRIPTION

Definitions

In order to more clearly understand the invention, the following definitions are provided:

Romaine Lettuce: Romaine lettuce is *Lactuca sativa* L. var. *longifolia* Lam; also known as Cos. The plant develops in an upright open or upright compact growing habit with coarse textured leaves. The leaves are longer than they are wide, cupping together to form an elongated loose head. Leaf margins are often entire or undulated, rarely frilled. Other leaves range in color from light green to dark green with a heavy midrib. Inner heart leaves are smaller and range from light yellow to light green in color.

Core Length: Core length is the length of the internal lettuce stem. Core length is measured from the base of the cut head to the tip of the core.

Core Diameter: Core diameter is the diameter of the lettuce stem at the base of the cut head.

Romaine Heart: Romaine heart is the densest part of the romaine plant often yellow and light green in color and of succulent texture. The heart is generally enclosed by two to three outer darker green leaves.

Heart Length: Heart length is the length of the vertically sliced lettuce plant as measured from the base of the cut stem to the top leaf margin of the longest outermost leaf that encloses the romaine heart.

Head Length: Core Length Ratio: The ratio of the head length to core length is indicative of the percentage of useable product produced by the lettuce plant.

Plant Diameter: The plant diameter is a measurement across the top of the lettuce plant at its widest point. The measurement of frame diameter is taken from the outer most leaf tip horizontally to the outer most leaf tip.

Head Weight: Head weight is the weight of the marketable lettuce plant, cut and trimmed to market specifications.

Rogueing: Rogueing is the process in lettuce seed production where undesired plants are removed from a variety. The plants are removed because they differ physically from the general desired expressed characteristics of the variety. The differences can be related to size, color, maturity, leaf texture, leaf margins, growth habit, or any other characteristic that distinguishes the plant.

Market Stage: Market stage is the stage when a lettuce plant is ready for commercial lettuce harvest. In the case of a romaine lettuce variety, a romaine plant is at a marketable state when the heart has some density and the head has reached an adequate size and weight.

PIC Type: PIC is an acronym for Paris Island Cos, a specific type and characterization of romaine lettuce. A PIC type romaine refers to an often vigorous growing romaine type with a smooth leaf surface. PIC type romaine varieties are often less heat resistant and faster growing than Florida type romaines.

Florida Type: A Florida type romaine refers to a specific class of romaine varieties with improved heat and bolting resistance, a more savoyed leaf surface, and corky root resistance. This class of romaine is often less vigorous and slower growing than the PIC type.

*Sclerotinia*: Two species of *Sclerotinia* infect lettuce in California and cause a disease known as lettuce drop: in coastal growing areas *Sclerotinia minor* is the primary species of importance, while in other areas *S. sclerotiorum* is more prevalent. *Sclerotinia minor* only infects the stems and leaves in contact with the soil. Once infection takes place, the fungus will cause a brown, soft decay that eventually destroys the plant crown tissue. Older leaves then wilt and later the entire plant will wilt and collapse, making it unharvestable. Plant collapse usually occurs when lettuce is near maturity. Profuse amounts of white mycelia and small (up to 0.125 inch or 3 mm), black, hard, resting bodies (sclerotia) form on the outside of the decayed crown.

*Sclerotinia sclerotiorum* can also infect lower leaves and stems, causing symptoms similar to those of *S. minor*. In addition, *S. sclerotiorum* has an aerial spore that can infect any of the upper leaves. Spores usually infect damaged or senescent tissue when the weather is cool and moist. Infection results in a watery, soft rot that is accompanied by white mycelial growth and formation of sclerotia. *Sclerotinia sclerotiorum* forms sclerotia that are larger (0.25-0.50 inch) than those of *S. minor.*

Sclerotia of both species enable the pathogens to survive in the soil for 2 to 3 years without susceptible hosts. Wet soil conditions favor disease development of both species. For *S. sclerotiorum*, cool and moist conditions are necessary for development of the fruiting structure (apothecium) that produces the airborne spores. In California, *S. minor* does not have a spore-producing stage. Symptoms caused by *Sclerotinia* species could resemble Verticillium wilt symptoms. The recent use of wider, 80-inch beds for lettuce production may cause lettuce drop from *S. minor* to be more severe because of increased bed moisture. In addition, the use of wider beds may be allowing *S. sclerotiorum* to increase in importance in the Salinas and other coastal valleys.

Tomato Bushy Stunt: Lettuce dieback was first observed in California in the mid-1980s, and reports of the disease have increased over the last 10 years. Complete crop losses have occurred in fields of romaine lettuce, and no commercial romaine cultivar has been shown to be resistant to the disease. In the U.S., romaine is a rapidly growing market segment, having increased 68% over the last five years (USDA, 2002). The disease has occurred in commercial fields of some leaf lettuce cultivars; however, symptoms have never been observed on any modern crisphead (iceberg) cultivars. Lettuce dieback is caused by several related Tombusviruses including Tomato Bushy Stunt virus (TBSV) and lettuce necrotic stunt virus (LNSV) (Liu et al., 1999; Obermeier et al., 2001). These are soilborne, highly stable, and mechanically transmitted, and have no known vector. The conditions affecting symptom development remain poorly understood. The disease is frequently observed in low-lying areas of fields with a prior history of flooding, suggesting that the virus may be carried in river water and/or that disease symptoms may be associated with increased root stresses such as those presented by excess moisture. No effective cultural or chemical control methods have yet been identified.

Corky Root: The pathogen responsible for corky root is *Rhizomonas suberifaciens*. CA1 is the most common strain and is publically available from the ATCC (accession No. 49355). Other useful strains include CA# and CA 15. Colonies of *R. suberifaceins* are initially translucent but later become opaque. The colonies are umbonate, compact colonies, which ultimately become wrinkled and have raised edges on S-medium as described in Van Bruggen, et al 1990, Host Range of *Rhizomonas suberifaciens*, the causal agent of corky root of lettuce. Plant Disease, 74:581-584.

*R. Suberifaciens* is an aerobic bacterium, ranging in morphology from small (0.6-1-4 u by 0.3-0.6 u) rods with one lateral flagellum to long filaments. According to KOH stringiness test, the bacteria seemed gram-positive, but with Hucker's gram-stain the bacteria stain gram-negative.

The type strain CA1 and other equivalent strains are publically available in the Salinas Valley of Calif. growing in the soil of lettuce fields. It is quite common and can be isolated using any suitable method known in the art, and characterized strains are conveniently available from Dr. Ariena Van Bruggen at the University of California and Davis.

Early symptoms of corky root are yellow bands on tap and lateral roots of lettuce seedlings. These yellow areas gradually expand, taking on a green-brown color and developing cracks and rough areas on the surface of the root. As disease severity increases, the entire taproot may become brown, severely cracked, and nonfunctional; the feeder root system will also be reduced and damaged. At this point, roots are very brittle and easily break off when examined. Corky root may cause internal discoloration of the root. When the root is severely diseased, aboveground symptoms consist of wilting during warm temperatures, stunting of plants, and general poor and uneven growth. Corky root symptoms could be confused with ammonium toxicity, which causes a brick-red discoloration of the central portion of the root and wilting of lettuce foliage.

The corky root bacterium, *Rhizomonas suberifaciens*, is a soilborne pathogen that is prevalent in most coastal lettuce growing areas but may not be present in inland regions. Corky root affects both leaf and head lettuce varieties. Disease is typically more severe when soil temperatures are warmer. Corky root is worse in fields where lettuce is grown consecutively. High soil nitrate levels can increase disease severity.

"Resistance to Tomato Bushy Stunt," "resistance to Tomato Bushy Stunt virus," or "resistance to TBSV" refers to a level of resistance in a lettuce variety as measured by visual symptoms. Resistance is deemed present when symptoms are not present in at least 80% of a lettuce variety when exposed to Tomato Bushy Stunt virus.

"Resistance to *Sclerotinia*," "resistance to *Sclerotinia minor*," or "resistance to *S. minor*" refers to leaf drop of lettuce or lettuce drop. A variety is considered resistant when greater than 80% of a variety is not visibly infected in a field harboring *S. minor* under weather conditions in which susceptible varieties, e.g., King Henry, exhibit about 90% infection.

Resistance to Corky Root is determined by PCR marker analysis. PCR marker analysis was done to determine the presence of the recessive cor gene. 10 plants of each test line were screened with the marker. All 10 plants of each of the test varieties showed the presence of the gene and were designated as resistant. As was the resistant control, PRO 1334. All 10 plants tested of the susceptible control showed the absence of the gene and were scored as susceptible. The parent variety PRO 1432, was scored as segregating for the gene as 6 of the plants were scored as resistant and 4 of the plants were scored as susceptible.

Taking into account these definitions, the present invention is directed to seeds of the lettuce variety 'Mondo', plants produced by growing 'Mondo' lettuce seeds, head isolated or harvested from the plants, one or more plants selected from a collection of 'Mondo' plants and seeds derived or produced there from; plants produced by crossing a lettuce plant with a 'Mondo' lettuce plant and seeds derived or produced there from.

Origin and Breeding History of the Variety 'Mondo'

'Mondo' is a tall and heavy PIC type romaine variety that forms dense heavy hearts and is adapted to the coastal production regions of California. This variety is distinct and unique to all other romaine lettuce varieties due to its combined disease and physiological resistances. 'Mondo' has a unique and valuable resistant resistance package, as it is resistant to Tomato Bushy Stunt virus, *Sclerotinia* and Corky root, three very problematic diseases found throughout the Salinas valley of Calif. In addition to these disease resistances, 'Mondo' is also resistant to the physiological problems associated with internal tip burn and fringe burn.

'Mondo' is a romaine lettuce variety developed from a hand pollinated cross of the Progeny Advanced Genetics proprietary breeding lines PRO 1432 and PRO 1334. The two parental varieties were selected for their specific disease and physiological resistances, and their respective yield potential.

PRO 1432 is a slightly savoyed and slow growing romaine variety with excellent densely formed heavy hearts and a low core. PRO 1432 is resistant to Tomato Bushy Stunt Virus, *Sclerotinia*, and segregates for 'cor', a marker associated with the presence of the recessive 'cor' gene which is responsible for corky root resistance. PRO 1432 is, however, highly susceptible to the physiological problems of internal tip burn and fringe burn. These two physiological issues are so significant in the market that the variety is not commercially viable.

PRO 1334, the pollen donating parent, was selected for its smooth PIC type leaf texture, its tall and vigorous growth habit, its densely formed and heavy hearts, and its tip burn and fringe burn resistance. PRO 1334 is also resistant to corky root rot, as indicated by the presence of the 'cor' gene.

The cross was made in Year 1, and through the single seed descent breeding method, we have developed a large and erect growing romaine variety with dense heavy hearts, well adapted to the coastal lettuce production regions of California. Through extensive field trialing and screenings 'Mondo' has demonstrated resistance to TBSV, *Sclerotinia*, corky root, tip burn and fringe burn.

In Year 1, in a summer research seed production field in the San Joaquin valley in Calif., a cross was made of the breeding line PRO 1432, designated as PSJV043137, with the breeding line PRO 1334, designated PSJV043138. The F1 seed was harvested in the fall of Year 1 and designated as PSJV043137×PSJV043138.

In late October of Year 1, forty F1 seeds of PSJV043137×PSJV043138 were planted in a green house facility in San Juan Bautista, Calif., indicated by research line number PSJB043659. At market maturity all apparent self pollinated plants were removed and the remaining F1 plants were allowed to self-pollinate. The F2 seed was then harvested in bulk in late April of Year 2. The seed was immediately cleaned, processed, blended, and prepared for planting.

Two hundred random F2 seeds of line number PSJB043659 were planted in a summer research seed production field and redesignated as PSJV053890. Segregation amongst the F2 population was noted and all plants were allowed to self pollinate and produce seed. The F3 seed from each plant was harvested and packaged individually in the fall of Year 2. One seed from each package (plant) was removed and placed in one envelope and designated as PAUS054549, and planted again in a research production field in Australia in October of Year 2. The research production field in Australia was observed, where segregation for phenotype and maturity was again evident and noted, and all plants were allowed to self-pollinate and produce seed. F4 seed from 100 individual plants was harvested, cleaned, and packaged individually. The packets were shipped from Australia to Salinas, Calif. for processing.

The 100 F4 lines, all from non-selected single F3 plants of the pedigree PSJV043137×PSJV043138, was processed in Salinas, Calif. in the summer of Year 3. A trial was prepared containing each of the 100 F4 individual lines of the designated pedigree, and an additional 200 lines from different pedigrees, using the parent varieties and susceptible and resistant standard varieties as checks for the multiple diseases. A research trial was planted in the Salinas valley in Calif. in spring of Year 4 in a field known to be infected with TBSV. The trial was evaluated in summer of Year 4. All F4 lines were evaluated based on phenotypic uniformity, improved size, improved weight, and improved tolerances to tip burn and fringe burn when compared to the parent and check varieties. The F4 lines were also rated on their resistance to TBSV. After multiple evaluations of the trial, 12 F4 lines of this pedigree were selected as they out performed the parent varieties, its sibs, and the majority of other lines in the trial for the designated traits. PAUS 054549-34 B/S was among the 12 F4 lines advanced.

The 12 F4 lines of this pedigree advanced, along with their parent lines, check varieties, and multiple other advanced lines from multiple pedigrees were trialed in 5 additional fields between July of Year 4 and May of Year 5. Three of the five fields were known to harbor TBSV, and two of the fields were known to harbor *Sclerotinia*. The F4 lines were screened for resistance to the diseases present, as well as tip burn and fringe burn. Yield traits such as weight, core length, plant height, and heart density were also evaluated. PAUS 054549-34 B/S continued to be resistant to TBSV and showed resistance to *Sclerotinia* in all trials, while being free of the symptoms associated with tip and fringe burn. This line also rated higher than most of its sibs for the yield traits measured.

Simultaneously with the trialing program, seed from these 12 items were also being increased. A sample of the remnant F4 seed from PAUS 054549-34 B/S, designated as PSJV086291, was planted in a research seed production field in May of Year 5. The block contained roughly 200 plants, which were rogued for phenotype and maturity at various stages of growth, all offtypes and variants were removed. The remaining plants in the block were allowed to self-pollinate, and the F5 seed from the block was harvested in mass.

The F5 stock seed was used to conduct an additional increase of PX 466 in a Year 5 commercial seed production crop grown in the San Joaquin valley in Calif. 100 individual plant selections were made from this seed production block to be used as the future stock seed for the variety. These 100 F6 plants were harvested and packaged individually in the fall of Year 5.

In the summer of Year 6, a trial was planted in the Salinas valley in Calif., containing all 100 individual plant selections and PX 466. The individual lines were evaluated at market maturity for uniformity and type relative to the PX 466 as well as core length, plant height, plant weight, tip burn and fringe burn. Line number PSJV466-68 was noted as being significantly taller than the PX 466 with more uniform size and height over all.

Simultaneous to the trial, 40 plants each of the 100 F6 individual plant selections were grown in a year 6 San Joaquin valley research and development seed production field, including PSJV466-68. The lines were rogued for type, and uniformity and the F7 seed was harvested from each line. The F7 generation of PSJV466-68 was redesignated with research number PSJV104725.

PSJV104725 was trialed on multiple occasions in the summer of Year 7, where it was continually taller than the PX 466, while maintaining all of the other selected traits. Based on these trial results, the variety was designated PX477 seed was increased in the fall of Year 7 in a southern hemisphere seed production planting. The F8 seed was harvested in early spring of Year 8, and named 'Mondo' in June of that year.

As evaluated in multiple seed production fields and commercial plantings for 2 generations (F7 and F8), 'Mondo' has been observed to be uniform and stable without variants.

As described in the Examples below, lettuce variety 'Mondo' has numerous distinguishing characteristics.

Breeding and Selection

The present invention is further directed to the use of 'Mondo' lettuce in breeding and selection of new varieties.

A. Breeding

In lettuce breeding, lines are selected for certain desired appropriate characteristics. For example, one line may be selected for bolt tolerance in the fall growing conditions of the desert production locations of California and Arizona or for resistance to viruses such as Tomato Bushy Stunt, *Sclerotinia* or Corky Root. Another line may be selected for the size, color and texture of the lettuce head. Crosses are made, for example, to produce a medium to light green, tip burn resistant romaine lettuce with improved texture, and size for spring and summer harvest in the Salinas Valley of Calif.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen is performed by procedures well known in the art of lettuce breeding.

The manual removal of anther tubes, though an effective means to ensure the removal of all self pollinating possibilities, is very tedious and time consuming when a large number of crosses are to be made. The breeders have therefore adapted a well documented and modified method of making crosses more efficiently using these methods. This particular cross was made by first misting the designated male flowers to wash the pollen off prior to fertilization. This process of misting is a proven and effective means of pollen removal that assures crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen is washed off with enough pressure to dislodge the pollen grains, but not enough to damage the style. Excess water is dried off with clean paper towels. About 30 minutes later, the styles should spring back up and the two lobes of the stigma are visibly open in a "V" shape. Pollen from another variety or donor parent is then introduced by gently rubbing the stigma and style of the donor parent to the maternal parent. Tags with the pertinent information on date and pedigree are then secured to the flowers in order to keep track.

About 3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two relevant references teaching methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908 both of which are hereby incorporated by reference in their entirety for the purpose of providing details on the techniques well known in the art. In the present invention, Para Cos and Frontier Cos were crossed.

B. Selection

In addition to crossing, selection may be used to identify and isolate new lettuce lines. In lettuce selection, lettuce seeds are planted, the plants are grown and single plant selections are made of plants with desired characteristics. Such characteristics may include improved head and frame size, deeper or darker green leaf color, etc. Seed from the single plant selections are harvested, separated from seeds of the other plants in the field and re-planted. The plants from the selected seed are monitored to determine if they exhibit the desired characteristics of the originally selected line. Selection work is continued over multiple generations to increase the uniformity of the new line.

Deposit Information

A deposit of the lettuce variety 'Mondo' is maintained by Progeny Advanced Genetics, having an address at 590A Works Street, Salinas, Calif. 93901, United States of America. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same variety with the American Type Culture Collection, (ATCC), P.O. Box 1549, MANASSAS, Va. 20108 USA.

At least 2500 seeds of lettuce variety 'Bondi' were deposited on Jun. 5, 2013 according to the Budapest Treaty in the American Type Culture Collection (ATCC), ATCC Patent Depository, 10801 University Boulevard, Manassas, Va., 20110, USA. The deposit has been assigned ATCC number PTA-120397. Access to this deposit will be available during the pendency of this application to persons determined by the Commissioner of Patents and Trademarks to be entitled thereto under 37 C.F.R. 1.14 and 35 U.S.C. 122. Upon allowance of any claims in this application, all restrictions on the availability to the public of the variety will be irrevocably removed.

The deposit will be maintained in the ATCC depository, which is a public depository, for a period of 30 years, or 5 years after the most recent request, or for the effective life of the patent, whichever is longer, and will be replaced if a deposit becomes nonviable during that period.

This invention will be better understood by reference to the following non-limiting Examples.

EXAMPLES

Example 1

General Trialing Method

The following steps illustrate the general trialing method of the invention:

I. Set Up

1. A trial is set up to compare one or more lines. Parental lines and related varieties are identified.
2. Primary slots are identified.
3. Accession lines are located and purchased/obtained from seed dealers or growers.
4. All varieties are assigned a number to maintain integrity and anonymity.
5. Trials are set up in with all necessary varieties. Variety arrangement for trial is diagramed.

II. Planting

1. Commercial plantings are located by contacting commercial growers during the planting slot recommended for the variety.
2. A field is located during commercial planting and the necessary rows and area is marked off.
3. Varieties are planted according to a diagram, generally in 100 foot ranges.
4. All varieties are planted in same manner to mimic the planting of the commercial variety as closely as possible.
5. A trial map is drawn diagramming the trial, the trial location in the field and directions to the field.

III. Maintenance

1. All varieties are treated identically. Plants are watered, fertilized, and treated to control pests in the same manner as other lettuce plants in the commercial field.
2. The trial is thinned to separate the plants for optimum growth.

IV. Evaluation

1. Evaluations are done as near to the time of the commercial harvest as possible.
2. The evaluation is conducted “blindly”. That is, the evaluator(s) do not have the key to the trial at the time of evaluation.
3. 24 heads of each variety are evaluated.

a. The frame diameter of 24 random plants are measured to the nearest cm.

b. 24 mature heads of each variety are cut to the cap leaf.

c. The heads are carried to an adequate work station d. The following measurements are then conducted and recorded:

1. Each head is weighed to the nearest gram.
2. The core diameter of each head is measured to the nearest mm.
3. The heads are then sliced in to halves, discarding 1 half.
4. The core lengths (from the cut stem to the core tip) are measured to the nearest mm.
5. The plant length (from the cut stem to the cap leaf) is measured to the nearest mm.
6. The plant diameter (at its widest point) is measured to the nearest mm.
7. The heart length is measured to the nearest mm.
8. The ideal maturity or harvest date is then estimated based on the solidity of the head, the core length and any other physiological characteristics present.
9. The leaf color is documented using the Munsell Color Charts for Plant Tissue.

e. From these measurements, an Excel program is used to calculate the averages, the standard deviations and the T-Tests for the compared varieties.

Example 2

Comparative Analysis

Following the procedures of Example 1, ‘Mondo’ romaine lettuce was compared to various other varieties. Comparative data was obtained and analyzed for different romaine lettuce lines. Core length, head length, and head weight as provided in the definitions section above were compared.

‘Mondo’ is a unique and distinct romaine lettuce variety with a medium to light green color and open to cupping growth habit compared to similar varieties. ‘Mondo’ has slow to medium growing and forms an open to very dense and heavy hearts.

The most distinguishing characteristics of ‘Mondo’ are the unique multiple resistances and improved adaptability to multiple end uses. ‘Mondo’ is resistant to the Tombusvirus known as Tomato Bushy Stunt Virus, *Sclerotinia*, and Corky Root.

TABLE 1

Results of PCR Analysis to Determine Corky Root Resistance

| | Corky Root Resistance based PCR analysis of individual plants | | |
|---|---|---|---|
| Plant No. | Mondo | PRO 1334 | PRO 1432 |
| 1 | Resistant | Resistant | Resistant |
| 2 | Resistant | Resistant | Resistant |
| 3 | Resistant | Resistant | Resistant |
| 4 | Resistant | Resistant | Resistant |
| 5 | Resistant | Resistant | Resistant |
| 6 | Resistant | Resistant | Susceptible |
| 7 | Resistant | Resistant | Susceptible |
| 8 | Resistant | Resistant | Susceptible |
| 9 | Resistant | Resistant | Susceptible |
| 10 | Resistant | Resistant | Susceptible |

Table 1 shows that based on PCR analysis for ‘cor’, the varieties ‘Mondo’ and PRO 1334 are homozygous recessive for the ‘cor’ gene, making the varieties resistant to corky root. PRO 1432 is homozygous dominant for ‘cor’, making it susceptible to the disease. Based on this analysis, PRO 1432 is segregating for the resistance.

Resistance to *Sclerotinia minor* was determined by growing the test variety (‘Mondo’) against known susceptible varieties in fields where *S. minor* is present, and under climate conditions where *S. minor* is known to thrive. Such conditions are when humidity levels are high and the average temperatures are between 55° F. and 65° F. The test plots were made as equivalent as possible using standard field plotting techniques and resistance is defined by visible infection. The symptoms are rotting or decaying basal portions of the plant. There is no practical survival or partial infection to provide relative scoring. The plants are either infected and scored with a ‘1’ and die, or not infected and scored with a ‘0’. The results are shown in Tables 2A and 2B.

TABLE 2A

| Trial | 1 | Trial | 2 | Trial | 3 |
|---|---|---|---|---|---|
| Map: | RSV08003 | Map: | RSV08021 | Map: | NA |
| Grower | D'Arrigo | Grower | D'Arrigo | Grower | D'Arrigo |
| Ranch | 25 Lot 31 | Ranch | 2 Lot 13 | Ranch | NA |
| Area | King City | Area | East Gonzalas | Area | Gonzalas |
| Wet Date | Feb. 6, Year 5 Green Forest | Wet Date | March 18, Year 5 Sun Belt | Wet Date | May 9, Year 5 Sun Belt |

| Plant | Mortality from Sclerotinia 'Mondo' | Sun Belt | Plant | Mortality from Sclerotinia 'Mondo' | Sun Belt | Plant | Mortality from Sclerotinia 'Mondo' | Sun Belt |
|---|---|---|---|---|---|---|---|---|
| 1 | 0 | 1 | 1 | 0 | 1 | 1 | 0 | 0 |
| 2 | 0 | 1 | 2 | 0 | 1 | 2 | 0 | 0 |
| 3 | 0 | 1 | 3 | 0 | 1 | 3 | 0 | 0 |
| 4 | 0 | 1 | 4 | 0 | 0 | 4 | 0 | 1 |
| 5 | 0 | 1 | 5 | 0 | 1 | 5 | 0 | 1 |
| 6 | 0 | 0 | 6 | 0 | 0 | 6 | 0 | 1 |
| 7 | 0 | 1 | 7 | 0 | 1 | 7 | 0 | 1 |
| 8 | 0 | 1 | 8 | 1 | 0 | 8 | 0 | 1 |
| 9 | 1 | 0 | 9 | 0 | 1 | 9 | 0 | 0 |
| 10 | 0 | 0 | 10 | 0 | 1 | 10 | 1 | 1 |
| 11 | 0 | 0 | 11 | 0 | 0 | 11 | 0 | 0 |
| 12 | 0 | 0 | 12 | 0 | 0 | 12 | 0 | 1 |
| 13 | 0 | 1 | 13 | 0 | 1 | 13 | 0 | 0 |
| 14 | 1 | 0 | 14 | 0 | 1 | 14 | 0 | 1 |
| 15 | 0 | 1 | 15 | 0 | 1 | 15 | 0 | 0 |
| 16 | 0 | 0 | 16 | 0 | 0 | 16 | 0 | 1 |
| 17 | 0 | 1 | 17 | 0 | 1 | 17 | 0 | 1 |
| 18 | 0 | 1 | 18 | 0 | 0 | 18 | 0 | 1 |
| 19 | 0 | 1 | 19 | 0 | 1 | 19 | 0 | 1 |
| 20 | 0 | 1 | 20 | 0 | 1 | 20 | 0 | 1 |
| 21 | 0 | 0 | 21 | 0 | 1 | 21 | 0 | 0 |
| 22 | 0 | 1 | 22 | 0 | 1 | 22 | 0 | 0 |
| 23 | 0 | 1 | 23 | 1 | 0 | 23 | 0 | 1 |
| 24 | 1 | 1 | 24 | 0 | 1 | 24 | 0 | 0 |
| 25 | 0 | 0 | 25 | 0 | 0 | 25 | 0 | 1 |
| 26 | 0 | 1 | 26 | 0 | 1 | 26 | 0 | 0 |
| 27 | 0 | 1 | 27 | 0 | 1 | 27 | 0 | 1 |
| 28 | 0 | 1 | 28 | 0 | 1 | 28 | 0 | 0 |

TABLE 2B

| Plant | Mortality from Sclerotinia 'Mondo' | Sun Belt | Plant | Mortality from Sclerotinia 'Mondo' | Sun Belt | Plant | Mortality from Sclerotinia 'Mondo' | Sun Belt |
|---|---|---|---|---|---|---|---|---|
| 29 | 0 | 1 | 29 | 0 | 1 | 29 | 0 | 1 |
| 30 | 0 | 0 | 30 | 0 | 0 | 30 | 0 | 1 |
| avg | 0.1 | 0.7 | avg | 0.07 | 0.67 | avg | 0.03 | 0.6 |
| std dev | 0.31 | 0.48 | std dev | 0.25 | 0.48 | std dev | 1.83E−01 | 4.98E−01 |
| ttest | 1.03312E−06 | | ttest | 1.09E−07 | | ttest | 2.42E−07 | |
| probability | 100.00 | | probability | 100.00 | | probability | 100.00 | |
| % Mortality | 10.0 | 66.7 | % Mortality | 6.7 | 66.7 | % Mortality | 3.3 | 60.0 |

Resistance to Tomato Bushy Stunt virus (TBSV) was determined by growing the test variety ('Mondo') against known susceptible varieties in fields where TBSV is present. The test plots were made as equivalent as possible using standard field plotting techniques and resistance is defined by visible infection. Infected plants can be severely stunted and mature, diseased plants may only reach 6 to 8 inches in height. The outermost leaves are extensively yellowed. The younger, inner leaves often remain dark green in color, but can be rough and leathery in texture. In some cases, the older leaves develop necrotic spotting that can turn into extensive areas of brown, dead tissue. There is no partial infection to provide relative scoring. The plants are either infected and scored with a '1' and die, or not infected and scored with a '0'. The results are shown in Table 3.

TABLE 3

| Plant | Mortality from TBSV 'Mondo' | Mortality from TBSV Sun Belt | Plant | Mortality from TBSV 'Mondo' | Mortality from TBSV Sun Belt |
|---|---|---|---|---|---|
| 1 | 0 | 1 | 1 | 1 | 1 |
| 2 | 0 | 1 | 2 | 0 | 1 |
| 3 | 0 | 1 | 3 | 0 | 1 |
| 4 | 0 | 0 | 4 | 0 | 1 |
| 5 | 0 | 0 | 5 | 0 | 1 |
| 6 | 0 | 0 | 6 | 0 | 1 |
| 7 | 0 | 1 | 7 | 0 | 1 |
| 8 | 0 | 1 | 8 | 0 | 1 |
| 9 | 0 | 1 | 9 | 0 | 1 |
| 10 | 0 | 1 | 10 | 0 | 0 |
| 11 | 1 | 1 | 11 | 0 | 0 |
| 12 | 0 | 0 | 12 | 0 | 0 |
| 13 | 0 | 0 | 13 | 0 | 1 |
| 14 | 0 | 0 | 14 | 0 | 1 |
| 15 | 0 | 1 | 15 | 1 | 1 |
| 16 | 1 | 0 | 16 | 0 | 1 |
| 17 | 0 | 1 | 17 | 0 | 0 |
| 18 | 0 | 1 | 18 | 0 | 1 |
| 19 | 0 | 1 | 19 | 0 | 1 |
| 20 | 0 | 1 | 20 | 0 | 1 |
| 21 | 0 | 1 | 21 | 0 | 0 |
| 22 | 0 | 0 | 22 | 0 | 1 |
| 23 | 0 | 0 | 23 | 0 | 0 |
| 24 | 0 | 1 | 24 | 0 | 1 |
| 25 | 0 | 1 | 25 | 0 | 1 |
| 26 | 0 | 1 | 26 | 0 | 0 |
| 27 | 0 | 1 | 27 | 0 | 1 |
| 28 | 0 | 1 | 28 | 0 | 1 |
| 29 | 0 | 0 | 29 | 0 | 1 |
| 30 | 0 | 1 | 30 | 0 | 1 |
| avg | 0.066666667 | 0.666666667 | avg | 0.066666667 | 0.766666667 |
| std dev | 0.253708132 | 8.652022533 | std dev | 0.253708132 | 0.430183067 |
| ttest | 1.09205E−07 | | ttest | 2.88674E−10 | |
| probability | 100.00 | | probability | 100.00 | |
| % Mortality | 6.7 | 66.7 | % Mortality | 6.7 | 76.7 |

'Mondo' most closely resembles the romaine variety 'Zuma', but is distinct by its a taller romaine heart, which developed to meet the market need for a taller romaine hear. The heart of 'Mondo' is consistently 4 to 5 centimeters longer than the heart of 'Zuma' as shown in the results listed in Table 4.

TABLE 4

| Trial | 1 | | Trial | 2 | | Trial | 3 | |
|---|---|---|---|---|---|---|---|---|
| Grower | D'Arrigo | | Grower | D'Arrigo | | Grower | Costa | |
| Ranch | 12-15 | | Ranch | 6-18 | | Ranch | Fano | |
| Area | Salinas | | Area | Gonzales | | Area | Gonzales | |
| Wet Date | February 24 | | Wet Date | March 6 | | Wet Date | March 7 | |
| | Plant Length (cm) | | | Plant Length (cm) | | | Plant Length (cm) | |
| Plant | 'Mondo' | 'Zuma' | Plant | 'Mondo' | 'Zuma' | Plant | 'Mondo' | 'Zuma' |
| 1 | 37 | 35 | 1 | 35 | 30 | 1 | 38 | 30 |
| 2 | 38 | 32 | 2 | 35 | 30 | 2 | 35 | 30 |
| 3 | 38 | 30 | 3 | 36 | 32 | 3 | 36 | 35 |
| 4 | 36 | 30 | 4 | 35 | 31 | 4 | 36 | 30 |
| 5 | 33 | 31 | 5 | 36 | 30 | 5 | 38 | 32 |
| 6 | 36 | 32 | 6 | 38 | 35 | 6 | 37 | 32 |
| 7 | 36 | 31 | 7 | 35 | 30 | 7 | 35 | 30 |
| 8 | 35 | 28 | 8 | 35 | 28 | 8 | 35 | 35 |
| 9 | 35 | 27 | 9 | 36 | 28 | 9 | 38 | 30 |
| 10 | 36 | 25 | 10 | 38 | 28 | 10 | 35 | 30 |
| 11 | 36 | 30 | 11 | 38 | 29 | 11 | 36 | 35 |
| 12 | 35 | 25 | 12 | 35 | 32 | 12 | 36 | 32 |
| 13 | 35 | 25 | 13 | 36 | 31 | 13 | 38 | 32 |
| 14 | 35 | 30 | 14 | 32 | 30 | 14 | 35 | 30 |
| 15 | 35 | 30 | 15 | 35 | 34 | 15 | 35 | 35 |
| 16 | 36 | 30 | 16 | 36 | 30 | 16 | 35 | 35 |
| 17 | 36 | 32 | 17 | 36 | 30 | 17 | 38 | 30 |
| 18 | 36 | 32 | 18 | 35 | 32 | 18 | 36 | 30 |
| 19 | 35 | 30 | 19 | 35 | 30 | 19 | 35 | 25 |
| 20 | 36 | 35 | 20 | 35 | 30 | 20 | 34 | 27 |

TABLE 4-continued

| | | | | | | | | |
|---|---|---|---|---|---|---|---|---|
| 21 | 35 | 30 | 21 | 35 | 35 | 21 | 35 | 28 |
| 22 | 35 | 30 | 22 | 38 | 30 | 22 | 35 | 30 |
| 23 | 34 | 35 | 23 | 35 | 30 | 23 | 38 | 32 |
| 24 | 36 | 32 | 24 | 34 | 25 | 24 | 35 | 35 |
| 25 | 36 | 32 | 25 | 33 | 28 | 25 | 32 | 30 |
| 26 | 38 | 32 | 26 | 35 | 27 | 26 | 36 | 35 |
| 27 | 36 | 30 | 27 | 35 | 35 | 27 | 36 | 36 |
| 28 | 35 | 35 | 28 | 38 | 30 | 28 | 35 | 32 |
| 29 | 35 | 30 | 29 | 35 | 30 | 29 | 34 | 35 |
| 30 | 35 | 30 | 30 | 38 | 35 | 30 | 32 | 30 |
| avg | 35.67 | 30.53 | avg | 35.60 | 30.50 | avg | 35.63 | 31.6 |
| std dev | 1.09 | 2.69 | std dev | 1.48 | 2.45 | std dev | 1.59E+00 | 2.76E+00 |
| t-test | 9.82222E−14 | | t-test | 7.10E−14 | | t-test | 3.75E−09 | |
| probability | 100.00 | | probability | 100.00 | | probability | 100.00 | |
| % Difference | −16.8 | | % Difference | −16.7 | | % Difference | −12.8 | |
| Confidence Interval | 0.012 | 0.031 | Confidence Interval | 0.017 | 0.028 | Confidence Interval | 0.018 | 0.032 |

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed:

1. *Lactuca sativa* seed designated as 'Mondo', representative sample of seed having been deposited under ATCC Accession Number PTA-120397.

2. A *Lactuca sativa* plant produced by growing the seed of claim 1.

3. A lettuce head isolated from the plant of claim 2.

4. A *Lactuca sativa* plant having all the physiological and morphological characteristics of the *Lactuca sativa* plant of claim 2.

5. An $F_1$ hybrid *Lactuca sativa* plant having 'Mondo' as a parent where 'Mondo' is grown from the seed of claim 1.

6. Pollen of the plant of claim 2.

7. An ovule of the plant of claim 2.

8. Tissue culture of the plant of claim 2.

9. A method of selecting lettuce, comprising:

a) growing more than one plant from the seed of claim 1; and b) selecting a plant from step a).

10. A *Lactuca sativa* plant selected by the method of claim 9.

11. *Lactuca sativa* seed produced from the *Lactuca sativa* plant of claim 10.

* * * * *